United States Patent
Reddy et al.

(10) Patent No.: US 9,770,437 B2
(45) Date of Patent: Sep. 26, 2017

(54) COMPOSITIONS OF ELTROMBOPAG

(71) Applicant: HETERO RESEARCH FOUNDATION, Hyderabad, Andhra Pradesh (IN)

(72) Inventors: Bandi Parthasaradhi Reddy, Andhra Pradesh (IN); Podili Khadgapathi, Andhra Pradesh (IN); Nelluri Ramarao, Andhra Pradesh (IN)

(73) Assignee: HETERO RESEARCH FOUNDATION, Hyderabad, Andhra Pradesh (IN)

( * ) Notice: Subject to any disclaimer, the term of this patent is extended or adjusted under 35 U.S.C. 154(b) by 0 days.

(21) Appl. No.: 14/915,714

(22) PCT Filed: Sep. 1, 2014

(86) PCT No.: PCT/IN2014/000565
§ 371 (c)(1),
(2) Date: Mar. 1, 2016

(87) PCT Pub. No.: WO2015/029074
PCT Pub. Date: Mar. 5, 2015

(65) Prior Publication Data
US 2016/0184268 A1   Jun. 30, 2016

(30) Foreign Application Priority Data

Sep. 2, 2013   (IN) .......................... 3914/CHE/2013

(51) Int. Cl.
*A61K 9/20* (2006.01)
*A61K 9/26* (2006.01)
*A61K 31/415* (2006.01)
*A61K 31/4152* (2006.01)

(52) U.S. Cl.
CPC ........ *A61K 31/4152* (2013.01); *A61K 9/2059* (2013.01); *A61K 9/2077* (2013.01); *A61K 9/2054* (2013.01)

(58) Field of Classification Search
CPC ... A61K 31/415; A61K 9/2054; A61K 9/2077
USPC .................................. 514/404; 424/464, 470
See application file for complete search history.

(56) References Cited

U.S. PATENT DOCUMENTS

| | | | |
|---|---|---|---|
| 7,160,870 B2 | 1/2007 | Duffy et al. | |
| 7,452,874 B2 | 11/2008 | Duffy et al. | |
| 7,473,686 B2 | 1/2009 | Duffy et al. | |
| 7,547,719 B2 | 6/2009 | Moore | |
| 8,052,994 B2 | 11/2011 | Muller et al. | |
| 2010/0129352 A1 | 5/2010 | Muller et al. | |

FOREIGN PATENT DOCUMENTS

WO    WO 2008136843 A1 * 11/2008 ......... A61K 31/4152

OTHER PUBLICATIONS

International Search Report and Written Opinion; International Application No. PCT/IN2014/000565; International Filing Date Sep. 1, 2014; dated Jan. 22, 2015; 8 pages.

* cited by examiner

*Primary Examiner* — Kevin E Weddington
(74) *Attorney, Agent, or Firm* — Cantor Colburn LLP

(57) ABSTRACT

The present invention relates to compositions of eltrombopag olamine. The present invention also relates to process for preparing compositions comprising eltrombopag olamine.

9 Claims, No Drawings

COMPOSITIONS OF ELTROMBOPAG

PRIORITY

This patent application is a §371 of PCT/IN/2014/000565, filed on Sep. 1, 2014 which claims priority to Indian patent application 3914/CHE/2013, filed on Sep. 2, 2013, under the provisions of 35 U.S.C. 119 and the International Convention for the protection of Industrial Property, the contents of which are incorporated by reference herein in their entirety.

FIELD OF THE DISCLOSURE

The present disclosure relates to pharmaceutical compositions comprising eltrombopag olamine and process for preparation thereof.

BACKGROUND

Eltrombopag olamine is chemically described as 3'-{(2Z)-2-[1-(3,4-dimethylphenyl)-3-methyl-5-oxo-1,5-dihydro-4H-pyrazol-4ylidene]hydrazino}-2'-hydroxy-3-biphenyl carboxylic acid-2-aminoethanol (1:2). Its empirical formula is $C_{25}H_{22}N_4O_4.2(C_2H_7NO)$, with structural formula as follows:

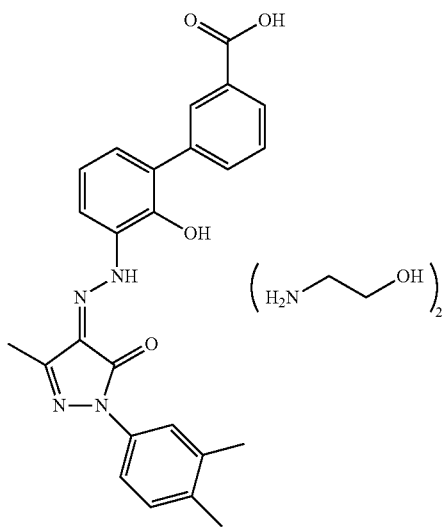

In the United States, eltrombopag olamine is available as oral tablets containing 12.5 mg, 25 mg, 50 mg and 75 mg eltrombopag, with trade name Promacta® by Glaxosmithkline.

U.S. Pat. Nos. 7,160,870, 7,452,874, 7,473,686 and 7,547,719 disclose eltrombopag and its salts.

U.S. Pat. No. 8,052,994 disclose eltrombopag olamine tablet composition comprising 40% drug-loaded granules and 4% to 12% by weight of an extragranular superdisintegrant based on total weight of tablet.

Accordingly, inventors of the present invention have developed compositions of eltrombopag olamine, that were found to be comparable with marketed Promacta® tablets.

SUMMARY

The present invention relates to solid dosage forms comprising eltrombopag olamine and one or more pharmaceutically acceptable excipients.

One embodiment of this, invention relates to pharmaceutical tablet composition comprising eltrombopag olamine, and a disintegrant in an amount of more than 12% by weight based on total weight of the composition.

Another embodiment of this invention relates to pharmaceutical tablet prepared by wet granulation process comprising eltrombopag olamine, microcrystalline cellulose and one or more pharmaceutical acceptable excipients; wherein said eltrombopag olamine comprise less than 40% by weight of granules.

Yet another embodiment of this invention relates to pharmaceutical tablet composition of eltrombopag olamine comprising an intragranular portion comprising eltrombopag olamine, microcrystalline cellulose, and an extragranular portion comprising microcrystalline cellulose and sodium starch glycolate in an amount of more than 12% by weight based on total weight of the composition, wherein said intragranular microcrystalline cellulose comprise 75 to 90% of total microcrystalline cellulose used in the composition.

Also included in the present invention is use of eltrombopag composition for treating thrombocytopenia.

DETAILED DESCRIPTION

The present invention relates to solid dosage forms comprising eltrombopag olamine and one or more pharmaceutically acceptable excipients. More particularly the present invention disclose pharmaceutical tablet compositions of eltrombopag olamine.

The term "active ingredient" or "active agent" or "drug" used interchangeably, is defined to mean active drug (e.g. eltrombopag olamine), that induce a desired pharmacological or physiological effect.

The term "pharmaceutically acceptable" as used herein means that which is useful in preparing a pharmaceutical composition that is generally safe and non-toxic.

The term "excipients" as used herein means a component of a pharmaceutical product that is not an active ingredient such as, for example, fillers, diluents, carriers and the like. The excipients that are useful in preparing a pharmaceutical composition are generally safe and non-toxic.

By the term "solid dosage form" or "dosage form" or "composition" as used herein refers to a solid dosage form suitable for administration, such as a tablet, capsule, spheroids, mini-tablets, pellets, granules, pills and the like.

As used in the specification and the appended claims, the singular forms "a", "an", and "the" include plural references unless the context clearly dictates otherwise. Thus for example, reference to "a method" includes one or more methods, and/or steps of the type described herein and/or which will become apparent to those persons skilled in the art upon reading this disclosure so forth.

The present invention relates to solid dosage forms comprising eltrombopag olamine and one or more pharmaceutically acceptable excipients and process for their preparation.

In one aspect, the present invention provides pharmaceutical composition comprising eltrombopag olamine and a disintegrant in an amount of more than 12% by weight based on total weight of the composition.

In another aspect, the present invention provides pharmaceutical tablet prepared by wet granulation process comprising eltrombopag olamine, microcrystalline cellulose and one or more pharmaceutical acceptable excipients; wherein said eltrombopag olamine comprise less than 40% by weight of granules.

Excipients of the present invention comprise diluents, disintegrants, binders, glidants, lubricants and combinations thereof.

The present invention comprise additional pharmaceutically acceptable diluents that include but are not limited to mannitol, isomalt, xylitol, sorbitol, pregelatinized starch, maize starch, potato starch, rice starch, wheat starch, powdered celluloses and the like and combinations thereof.

The present invention provides solid dosage forms comprising eltrombopag olamine as an active agent, microcrystalline cellulose and at least one disintegrant selected from sodium starch glycolate, croscarmellose sodium, crospovidone, polacrilin potassium and low substituted hydroxypropyl cellulose.

Preferable concentration of disintegrant used according to the present invention is 13% to 20% by weight relative to the total weight of the composition.

Binders according to the present invention include but are not limited to polyvinyl pyrrolidone, copovidone, hydroxypropyl cellulose, hydroxypropyl methylcellulose, pregelatinized starch, powdered acacia, gelatin, guar gum, carbomers and the like, and combinations thereof.

Glidants according to the present invention include but are not limited to colloidal silicon dioxide, magnesium silicate, magnesium trisilicate, talc, and other forms of silicon dioxide, such as aggregated silicates and hydrated silica and the like, and combinations thereof.

Lubricants according to the present invention include but are not limited to magnesium stearate, aluminium stearate, sucrose stearate, stearic acid, talc, fumaric acid, palmitic acid, sodium stearyl fumarate, glyceryl monostearate, carnauba wax, hydrogenated vegetable oils, mineral oil, polyethylene glycols and the like and combinations thereof.

In particular, pharmaceutical tablet composition of eltrombopag olamine comprising an intragranular portion comprising eltrombopag olamine, microcrystalline cellulose, and an extragranular portion comprising microcrystalline cellulose and sodium starch glycolate in an amount of more than 12% by weight based on total weight of the composition, wherein said intragranular microcrystalline cellulose comprise 75 to 90% of total microcrystalline cellulose used in the composition.

Tablets of the present invention are prepared by wet granulation technique which include steps of sifting of the powder components through sieve of desired mesh size, dry mixing the components in rapid mixer granulator, addition of binding agent and thus granulating the components, drying the granules, blending of dried granules by addition of extragranular components, lubricating using desired lubricants and finally compressing the blend into tablets of desired properties.

Tablets of the present invention are coated with an aqueous film coating composition.

A film coat on the tablet provides an elegant appearance, protect from moisture and further contributes to the ease with which it can be swallowed.

Solid dosage forms of the present invention comprising therapeutically effective amount of eltrombopag are useful for the treatment of thrombocytopenia.

EXAMPLES

The following examples further describe and demonstrate particular embodiments within the scope of the present invention. The examples are given solely for illustration and are not to be construed as limitations as many variations are possible without departing from spirit and scope of the invention.

Example 1

TABLE 1

Tablet compositions of Eltrombopag olamine

| Ingredients | mg/tab |
|---|---|
| Dry mix: | |
| Eltrombopag olamine* | 63.80 |
| Microcrystalline cellulose | 134.30 |
| Mannitol | 59.50 |
| Povidone | 6.40 |
| Binder solution: | |
| Purified water | q.s |
| Extragranular ingredients: | |
| Microcrystalline cellulose | 30.00 |
| Sodium starch glycolate | 52.50 |
| Lubrication: | |
| Magnesium stearate | 3.500 |
| Core tablet weight | 350.00 |
| Film coating: | |
| Opadry ® blue | 14.00 |
| Purified water | q.s. |
| Total tablet weight | 364.00 |

*63.80 mg of eltrombopag olamine is equivalent to 50 mg of eltrombopag.

Preparation Method
1. Eltrombopag olamine was sifted through mesh #30 sieve,
2. microcrystalline cellulose, mannitol, povidone were sifted together through mesh #40 sieve.
3. sifted materials of step 1 and 2 were sifted together through mesh #30 sieve and blended for 10 minutes,
4. blend of step 3 was granulated using purified water, followed by drying and sifting to get the desired granules,
5. extragranular microcrystalline cellulose, Sodium starch glycolate were sifted together through mesh #40 sieve,
6. granules of step 4 were blended with blend of step 5,
7. extragranular magnesium stearate was sifted through mesh #60 sieve,
8. blended granules of step 6, were lubricated with magnesium stearate of step 7,
9. lubricated blend of step 8 was compressed into tablets,
10. tablets of step 9 were film coated using Opadry® blue dispersion.

Example 2

TABLE 2

Tablet compositions of Eltrombopag olamine

| Ingredients | mg/tab |
|---|---|
| Granules, 24% drug loaded | (264.00) |
| Eltrombopag olamine* | 63.80 |
| Microcrystalline cellulose | 140.70 |
| Mannitol | 59.50 |
| Purified water | q.s |
| Extragranular ingredients: | |

TABLE 2-continued

Tablet compositions of Eltrombopag olamine

| Ingredients | mg/tab |
|---|---|
| Microcrystalline cellulose | 30.00 |
| Sodium starch glycolate | 52.50 |
| Lubrication: | |
| Magnesium stearate | 3.50 |
| Core tablet weight | 350.00 |
| Film coating: | |
| Opadry ® blue | 14.00 |
| Purified water | q.s. |
| Total tablet weight | 364.00 |

*63.80 mg of eltrombopag olamine is equivalent to 50 mg of eltrombopag.

Preparation Method
1. Preparation of 24% drug loaded granules:
i). Eltrombopag olamine was sifted through mesh #30 sieve,
ii). microcrystalline cellulose, mannitol were sifted together through mesh #40 sieve,
iii). sifted materials of step i and ii were sifted together through mesh #30 sieve and blended for 10 minutes,
iv). blend of step iii was granulated using purified water, followed by drying and sifting to get the desired granules,
2. extragranular microcrystalline cellulose, sodium starch glycolate were sifted together through mesh #40 sieve,
3. granules of step 1 were blended with blend of step 2,
4. extragranular magnesium stearate was sifted through mesh #60 sieve,
5. blended granules of step 3, were lubricated with magnesium stearate of step 4,
6. lubricated blend of step 5 was compressed into tablets,
7. tablets of step 6 were film coated using Opadry® blue dispersion.

Example 3

TABLE 3

Tablet compositions of Eltrombopag olamine

| Ingredients | mg/tab |
|---|---|
| Granules, 36% drug loaded | (261.50) |
| Eltrombopag olamine* | 95.70 |
| Microcrystalline cellulose | 102.40 |
| Mannitol | 57.00 |
| Povidone | 6.40 |
| Purified water | q.s |
| Extragranular ingredients: | |
| Microcrystalline cellulose | 30.00 |
| Sodium starch glycolate | 51.50 |
| Colloidal silicon dioxide | 3.50 |
| Lubrication: | |
| Magnesium stearate | 3.50 |
| Core tablet weight | 350.00 |
| Film coating: | |
| Opadry ® pink | 14.00 |
| Purified water | q.s. |
| Total tablet weight | 364.00 |

*95.70 mg of eltrombopag olamine is equivalent to 75 mg of eltrombopag.

Preparation Method

1. Preparation of 36% drug loaded granules:
i). Eltrombopag olamine was sifted together through mesh #30 sieve,
ii). microcrystalline cellulose, mannitol and povidone were sifted together through mesh #40 sieve,
iii). sifted materials of step i and ii were sifted together through mesh #30 sieve and blended for 10 minutes,
iv). blend of step iii was granulated using purified water, followed by drying and sifting to get the desired granules,
2. extragranular microcrystalline cellulose, Sodium starch glycolate and Colloidal silicon dioxide together were sifted through mesh #40 sieve,
3. granules of step 1 were blended with blend of step 2,
4. extragranular magnesium stearate was sifted through mesh #60 sieve,
5. blended granules of step 3, were lubricated with magnesium stearate of step 4,
6. lubricated blend of step 5 was compressed into tablets,
7. tablets of step 6 were film coated using Opadry® pink dispersion.

Comparative Study on Dissolution

Dissolution test was performed for tablets prepared as per Example 1 and Promacta 50 mg tablets, using USP apparatus II, 50 rpm, in 900 ml of pH 6.8 phosphate buffer containing 0.5% polysorbate 80.

TABLE 4

| | Time in minutes | | | | | |
|---|---|---|---|---|---|---|
| | 5 min | 10 min | 15 min | 30 min | 45 min | 60 min |
| Example-1 Dissolution (%) | 33 | 66 | 83 | 95 | 96 | 96 |
| Promacta 50 mg tablets Dissolution (%) | 22 | 49 | 65 | 83 | 88 | 89 |

Based on results presented in Table 4, inventive Example 1 showed comparable dissolution properties with Promacta 50 mg tablets.

We claim:

1. A pharmaceutical tablet composition comprising eltrombopag olamine and a disintegrant, wherein the disintegrant is present in an amount of greater than 12% by weight based on a total weight of the composition.

2. The tablet composition according to claim 1, wherein said disintegrant is present in an amount of 13% to 20% by weight based on the total weight of the composition.

3. The tablet composition according to claim 1, wherein said disintegrant is sodium starch glycolate, croscarmellose sodium, crospovidone, polacrilin potassium, low substituted hydroxypropyl cellulose, or a combination thereof.

4. The tablet composition according to claim 1, wherein said disintegrant is sodium starch glycolate.

5. The tablet composition according to claim 1, further comprising microcrystalline cellulose.

6. A pharmaceutical tablet according to claim 1, wherein the eltrombopag olamine is in the form of granules prepared by a wet granulation process, the granules comprising the eltrombopag olamine, microcrystalline cellulose and one or more pharmaceutically acceptable excipients; wherein said eltrombopag olamine comprises less than 40% by weight of the granules.

7. The tablet of claim 6, wherein said eltrombopag olamine comprises 10% to 38% by weight of the granules.

8. A pharmaceutical tablet composition of eltrombopag olamine comprising:
   (a) an intragranular portion comprising eltrombopag olamine, and intragranular microcrystalline cellulose, and
   (b) an extragranular portion comprising extragranular microcrystalline cellulose and sodium starch glycolate in an amount of greater than 12% by weight based on a total weight of the composition,
   wherein said intragranular microcrystalline cellulose comprises 75 to 90% of the total microcrystalline cellulose used in the composition.

9. The tablet composition according to claim 8, wherein said sodium starch glycolate is present in an amount of 13% to 20% by weight based on the total weight of the composition.

* * * * *